United States Patent [19]

Odenwälder et al.

[11] 4,174,969
[45] Nov. 20, 1979

[54] LIGHT SENSITIVE PHOTOGRAPHIC MATERIAL

[75] Inventors: Heinrich Odenwälder, Cologne; Erwin Ranz, Leverkusen, both of Fed. Rep. of Germany

[73] Assignee: AGFA-Gevaert, A.G., Leverkusen, Fed. Rep. of Germany

[21] Appl. No.: 787,970

[22] Filed: Apr. 15, 1977

[30] Foreign Application Priority Data

Apr. 21, 1976 [DE] Fed. Rep. of Germany ....... 2617310

[51] Int. Cl.$^2$ .......................... G03C 7/00; G03C 1/40
[52] U.S. Cl. .................... 430/445; 430/382; 430/544; 430/566; 430/957
[58] Field of Search ...................... 96/55, 95, 66.3, 76, 96/77, 100, 56.3, 56.4, 56.5

[56] References Cited

U.S. PATENT DOCUMENTS

| | | | |
|---|---|---|---|
| 3,227,554 | 1/1966 | Barr et al. | 96/95 |
| 3,938,996 | 2/1976 | Fujiwhara et al. | 96/66.3 |
| 3,958,993 | 5/1976 | Fujiwhara et al. | 96/66.3 |
| 3,961,959 | 6/1976 | Fujiwhara et al. | 96/95 |
| 4,046,574 | 9/1977 | Odenwalder et al. | 96/77 |

*Primary Examiner*—Travis Brown

[57] ABSTRACT

For controlling in a color photographic material the gradation, graininess, sharpness, edge and interimage effect and thus improving the overall color reproduction thioether DIR compounds of the following formula are particularly useful:

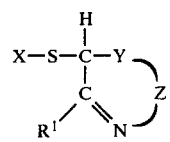

in which X is a group that if split off together with the sulfur atom forms a diffusing development inhibiting mercaptan, Y represents —O—,

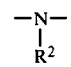

or —S—, Z represents the ring members completing a 6-membered heterocyclic ring, $R^1$ is an aliphatic, araliphatic or aromatic hydrocarbon group, a heterocyclic group or acyl, and $R^2$ is the same as $R^1$ or hydrogen.

5 Claims, No Drawings

LIGHT SENSITIVE PHOTOGRAPHIC MATERIAL

This invention relates to a photographic material containing compounds which react with oxidation products of colour developer components to release diffusing substances, capable of inhibiting the development of silver halide.

It is known to incorporate in colour photographic materials compounds which release silver halide development inhibitors in their reaction with colour developer oxidation products. Compounds of this kind include, for example, the so-called DIR couplers (DIR=-development-inhibitor-releasing) which have been described in U.S. Pat. No. 3,227,554 or the so-called DIR compounds described in U.S. Pat. No. 3,632,345.

These DIR couplers and DIR compounds generally contain, in their coupling position, a thioether substituent which during or following the reaction with the oxidized colour developer, is split off to form a diffusible mercapto compound which has development inhibiting properties and can therefore influence subsequent development of the silver halide. The properties of photographic materials can be improved in several respects by using such DIR couplers or compounds. The graininess, sharpness and gradation can be controlled by means of such compounds and a substantial improvement in colour reproduction as a whole can thereby be obtained. Reference should be made in this connection to the article entitled "Development-Inhibitor-Releasing Couplers in Photography" in "Photographic Science and Engineering" 13, 74(1969).

The known DIR couplers inevitably give rise to a dye in addition to the released development inhibitor. The known DIR-compounds such as those disclosed in the above mentioned U.S. Pat. No. 3,632,345 or in German Offenlegungsschriften Nos. 2 359 295, 2 362 752, 2 405 442, 2 448 063, 2 540 959 and 2 552 505 give rise to substantially colorless compounds in their reaction with oxidized color developer.

It has been found, however, that most of the known DIR-compounds are either too unstable or insufficiently reactive under certain operating conditions. In the former case the development inhibitor is not liberated in accordance with the image, a fact which manifests itself as a general loss in sensitivity. In the latter case the inhibitor is split off too slowly and therefore cannot intervene to a sufficient extent in the development process. Among the known DIR-couplers and DIR-compounds, many of those which are sufficiently stable in photographic layers to release the development inhibitor image-wise are generally not sufficiently reactive to influence the gradation, graininess, sharpness and interimage effects as desired. Also it has turned out very recently that for particular purposes the DIR-compounds should have a certain exactly graduated reactivity and that, therefore, it would be desired to have at hand a great number of DIR-compounds of graduated reactivity.

It is therefore an object of the present invention to find new compounds which, when reacted with color developer oxidation products, release development inhibiting substances which are sufficiently stable but, at the same time also sufficiently reactive, to produce a high edge effect and interimage effect and straighten the gradation curve.

According to the invention, this problem is solved by providing new DIR-compounds.

The invention relates to a color photographic material which contains, in at least one silver halide emulsion layer or in a light insensitive layer or binder associated therewith, a thioether compound which is preferably non-diffusible and which reacts with the oxidation product of a color developer substance containing a primary aromatic amino group to release a diffusible substance which inhibits development of the silver halide.

The material of the present invention contains a thioether compound of the following Formula I:

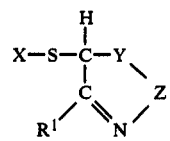

in which

X represents an aliphatic group, an aromatic group or in particular, a heterocyclic group such that when it is split off together with the sulfur atom of the thioether bridge it forms a diffusible mercapto compound which inhibits the development of silver halide;

Y represents —O—,

or S;

Z represents the ring members required for completing a 6-membered heterocyclic ring, which ring may have fused to it a saturated or unsaturated carbocyclic or heterocyclic ring, for example Z may be the ring members required for completing a 6H-1,3,4-thiadiazine, a 2H-1,4-benzoxazine, a 2H-1,4-benzodiazine, a 2H-1,4-benzothiazine, a 7H-s-triazolo[3,4-b]-1,3,4-thiadiazine or a 4H,8H-as-triazino[3,4-b]-1,3,4-thiadiazin-4-one.

The above mentioned ring members may be substituted by any groups familiar to the expert in the art as conventional substituents found in the chemistry of DIR-couplers and DIR-compounds, provided that they are photographically inert. Examples include hydrogen, aliphatic, araliphatic or aromatic hydrocarbon groups which may in turn carry substituents; also acyl such as alkylcarbonyl, or thioether groups such as the group —SX;

R¹ represents an aliphatic, araliphatic or aromatic hydrocarbon group which may be substituted, or a saturated or unsaturated heterocyclic group or acyl such as alkylcarbonyl, or alkoxycarbonyl;

R² represents hydrogen, an aliphatic, araliphatic or aromatic hydrocarbon group or acyl.

Examples of particularly preferred thioether compounds according to the present invention are presented by compounds of the following Formula II or tautomers thereof:

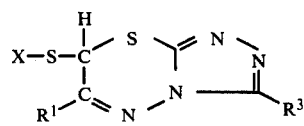

in which X and R¹ have the meanings specified above and R³ may have the meaning given for R¹ or it may represent hydrogen or a thioether group, e.g. the group —SX.

Examples of aliphatic groups which X may represent include alkyl groups having 1 to 10 carbon atoms which may be substituted by carboxyl and/or amino groups, e.g. CH₂—COOH and

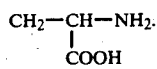

Examples of aromatic groups which X may represent include phenyl and naphthyl groups which may be substituted, such as phenyl, carboxyphenyl, or nitrophenyl.

Examples of heterocyclic groups which X may represent include the following:

5-membered or 6-membered heteroaromatic groups having at least one nitrogen atom, e.g.
   tetrazolyl, such as 1-phenyltetrazolyl, 1-nitrophenyltetrazolyl, or 1-naphthyltetrazolyl;
   triazolyl such as 1-phenyl-1,2,4-triazolyl;
   thiadiazolyl such as 2-phenylamino-1,3,4-thiadiazolyl, oxadiazolyl;
   thiazolyl including benzothiazolyl and naphthothiazolyl;
   oxazolyl, including benzoxazolyl and naphthoxazolyl, for example 7-sulphonaphtho-[2,3-d]-oxazolyl;
   pyrimidyl, such as 4-methyl-6-aminopyrimidyl or 4-methyl-6-hydroxy-pyrimidyl or
   triazinyl such as thiadiazolotriazinyl.

Compounds in which X represents a 1-phenyltetrazolyl group have proved to be particularly useful.

Acyl groups which are represented by the substituents R¹, R² and R³ or which are contained in these substituents are derived from aliphatic or aromatic carboxylic or sulphonic acid, e.g. alkylcarbonyl such as acetyl or octadecanoyl, alkylsulphonyl such as hexadecylsulphonyl, aroyl such as benzoyl, arylsulphonyl such as p-tolylsulphonyl or the semiesters of carbonic acid such as alkoxycarbonyl.

Aliphatic groups which are represented by the substituents R¹, R² and R³ or contained in these substituents include straight or branched chain alkyl groups having up to 22 carbon atoms, e.g. methyl, ethyl, isopropyl, n-butyl, pentadecyl or octadecyl. The alkyl groups may in turn contain substituents, e.g. hydroxyl, alkoxy, halogen, carboxyl, sulphonyl or aryl.

In the latter case, the alkyl groups are also referred to as aralkyl groups, e.g. benzyl or phenylethyl.

Aromatic groups represented by the substituents R¹, R² and R³ include, for example, phenyl and naphthyl groups, and these may in turn carry substituents.

R¹ preferably represents an alkyl, aryl, heterocyclic or acyl group.

It is preferred to use compounds in which at least one of the groups R¹, R² and R³ contains a photographically inert group which confers diffusion resistance.

Groups which confer diffusion resistance are groups which make it possible for the compounds according to the invention to be incorporated in a diffusion resistant form in the hydrophilic colloids conventionally used in photographic materials. Groups particularly suitable for this purpose are organic groups generally containing straight or branched chain aliphatic groups and which may also contain isocyclic or heterocyclic aromatic groups. The aliphatic portion of these groups generally contains from 8 to 20 carbon atoms. These groups are attached to the remainder of the molecule either directly or indirectly, e.g. via one of the following groups: —CONH—, —SO₂NH—, —CO—, —SO₂—, —O—, —S— or —NR'— in which R' represents hydrogen or alkyl.

The group which confers diffusion resistance or one of the other groups may, in addition, contain groups which confer solubility in water, e.g. sulpho groups or carboxyl groups, and these groups may also be present in an anionic form.

Since the diffusion properties depend on the molecular size of the compound as a whole, it is sufficient in some cases, for example when the molecule as a whole is large enough, to use one or more shorter chained groups such as tertiary butyl, cyclopentyl or isoamyl for conferring diffusion resistance.

The following are examples of thioether compounds of the general formula I. In the formulae 1 to 7 X represents the 1-phenyl-5-tetrazolyl group.

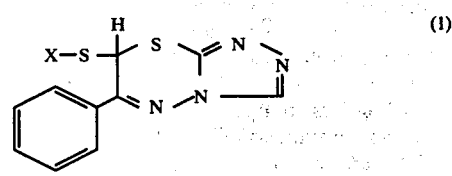

(1)

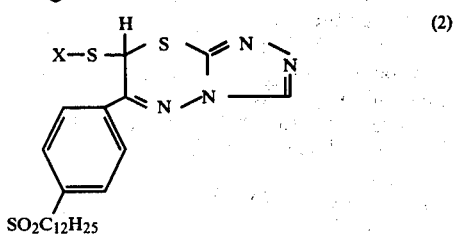

(2)

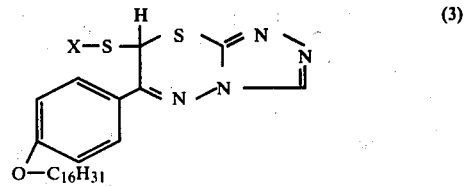

(3)

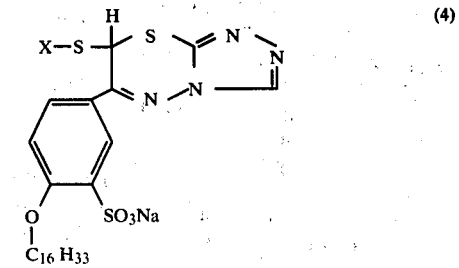

(4)

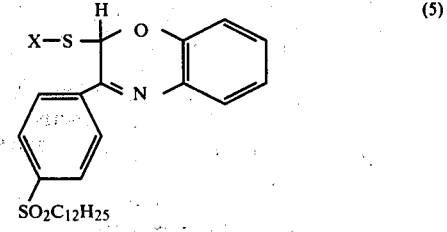

(5)

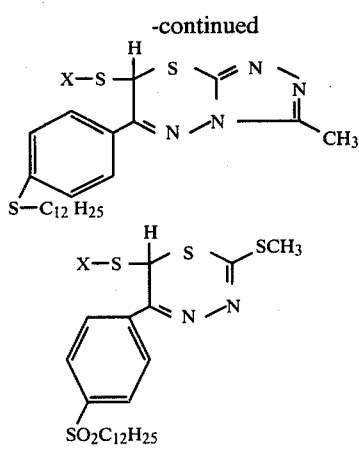

Preparation of the DIR compounds according to the present invention may be carried out by two methods:
1. Cyclisation of an α-halogen ketone of the formula $R^1$—CO—$CH_2$-halogen with an amine of the formula $H_2N$—Z—YH to form an intermediate product of the formula

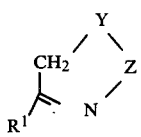

as described, for example, in Z.Chem. 9, 111 (1969), in which formula $R^1$, Y and Z have the meaning indicated above. This intermediate product is subsequently halogenated in the methylene group and then reacted with the metal salt of a mercapto compound to produce the desired DIR compound.

2. The alternative method consists of cyclising the α-halogen α-mercapto-substituted ketone with the amine previously mentioned.

Each of the two methods of preparation will be described below with the aid of an example.

Preparation of compound 2 (Method of preparation 1)

1.16 g of 4-amino-3-mercapto-1,2,4-triazole and 4.31 g of 2-bromo-1-[4-dodecylsulphonylphenyl]-ethanone-1 in 50 ml of ethanol are boiled under reflux for one hour. The precipitate obtained on cooling is suction filtered and recrystallised from methanol.

The yield was 3.5 g and the product had a melting point of 165° to 167° C.

1.6 ml of sulphuryl chloride are added dropwise at 50° C. to a solution of 8.8 g of the previously prepared compound in 50 ml of ethylene chloride and the mixture is stirred for 30 minutes at 50° C. After the addition of 4.0 g of sodium-1-phenyl-5-tetrazolyl mercaptide, the reaction mixture is vigorously stirred for 2 hours and adjusted to pH 8 by the addition of 2 N NaOH solution.

The organic phase is then separated off and concentration by evaporation and the residue is stirred up with methanol. The resulting precipitate is suction filtered and recrystallised from methanol. The yield is 7.2 g, and the melting point is, 158° to 159° C., with decomposition.

Preparation of compound 4 (method of preparation 2)

23.3 g of the sodium salt of 2(1-phenyl-5-tetrazolylthio)-1-[4-cetyloxy-3-sulphophenyl]-ethanone-1 are dissolved in 110 ml of glacial acetic acid at 60° to 70° C. After the addition of 1.83 ml of bromine, a sample of the mixture is removed and heated until decolorised to start bromination and returned to the reaction mixture. After 15 minutes' stirring each at 60° C. and then at 70° C., the reaction mixture is cooled and 5.9 g of sodium acetate are added to it. 110 ml of water are then added dropwise over a period of one hour and the resulting precipitate is suction filtered. The compound obtained in this way is dissolved in 135 ml of isopropanol at 60° C. 4.2 g of 4-amino-3-mercapto-1,2,4-triazole are added to the solution and the reaction mixture is heated under reflux for one hour. After addition of a further 3.3 g of sodium acetate, the reaction mixture is stirred overnight and the resulting precipitate is then suction filtered and washed with 80 ml of isopropanol. The yield is 16 g and the melting point is 166° C. with decomposition.

Compounds according to the invention having the formula I in which Y represents S can be prepared in a similar manner.

Compounds according to the invention of formula I in which Y represents $NR^2$ or O can be prepared by suitably modified processes.

Preparation of the corresponding heterocyclic compounds with unsubstituted methylene groups has been described in the literature, for example the preparation of compounds in which Y represents $NR^2$ has been described in J. Org. Chem. 27, 3734 (1962) and the preparation of compounds in which Y represents O in Chem. Ber. 23, 173.

The compounds according to the invention are comparable with the known DIR couplers and DIR compounds in that, like them, they are non-diffusible thioether compounds which react with colour developer oxidation products to split off a diffusible mercaptan which inhibits development of the silver halide. According to U.S. Pat. No. 3,148,062, DIR-couplers are subdivided into those in which the releasable group already has an inhibitory action before coupling and those in which the inhibitory action occurs only when a molecular grouping is split from the coupling position. In the latter case, the inhibitor is non-preformed. According to this terminology, the compounds according to the invention should also be described as non-diffusible compounds which react with colour developer oxidation products to release a diffusible, non-preformed development inhibitor.

The compounds according to the invention are ditinguished from the known DIR couplers and DIR compounds by their higher reactivity so that by using the compounds according to the invention in photographic materials the control of the gradation, graininess and sharpness and the edge and interimage effects can advantageously be improved.

The DIR compounds according to the invention are particularly useful for obtaining high edge effects and interimage effects.

The DIR compounds according to the invention may be used particularly in those colour photographic multilayered materials in which the silver halide is developed by the usual colour developers after imagewise exposure, for example by the usual aromatic compounds based on p-phenylenediamine and containing at least one primary amino group.

The following are examples of suitable colour developers:

N,N-Dimethyl-p-phenylenediamine;

N,N-diethyl-p-phenylenediamine;
monomethyl-p-phenylenediamine;
2-amino-5-diethylaminotoluene;
N-butyl-N-ω-sulphobutyl-p-phenylenediamine;
2-amino-5-(N-ethyl-N-β-methanesulphonamidoethylamino)-toluene;
N-ethyl-N-(β-hydroxyethyl)-p-phenylenediamine;
N,N-bis-(β-hydroxyethyl)-p-phenylenediamine;
2-amino-5-(N-ethyl-N-β-hydroxyethylamino)-toluene
and the like.

Other suitable colour developers have been described, for example, in J. Amer. Chem. Soc. 73, 3100 (1951).

The developer compounds are usually contained in an alkaline development bath which is used for treating the colour photographic material after it has been exposed imagewise but it is also possible to incorporate the compound in one or more layers of the photographic material. In that case, the developer compounds may contain groups which render them diffusion resistant and they may be situated in a layer which also contains a diffusion resistant colour coupler or a diffusion resistant dye-giving compound, as described, for example, in U.S. Pat. No. 3,705,035.

Development then requires only an alkaline activator solution containing an auxiliary developer such, for example, as phenidone. The oxidation product obtained from the colour developer during development reacts with the non-diffusible colour coupler to form a non-diffusible image dye. At the same time, the oxidation product of the colour developer reacts with the non-diffusible DIR compounds of the invention which are also present, to liberate diffusible inhibitor substances.

The colour photographic multilayered material according to the invention contains a compound of the formula I in at least one of its layers. This DIR compound may be incorporated in a light-sensitive silver halide emulsion layer or in a hydrophilic layer of binder which is associated with such a light-sensitive silver halide emulsion layer and need not itself be light sensitive. The term "associated" is used in this context to describe a layer which is in such spatial relationship to the light-sensitive silver halide emulsion layer that, when development of the silver halide emulsion layer takes place, significant quantities of colour developer oxidation products occur in the associated layer due to diffusion from the light-sensitive silver halide emulsion layer.

The concentration of DIR compound according to the invention in its layer may be varied within wide limits, for example between $0.1 \times 10^{-3}$ and $40 \times 10^{-3}$ mol per kg of silver halide emulsion while, in the associated layers of binder, it may vary e.g. between $0.1 \times 10^{-3}$ and $10 \times 10^{-3}$ mol per gram of binder. The concentration depends on the particular purpose for which the material is required, on the particular silver halide emulsion used and on whether the DIR compound is situated in a silver halide emulsion layer or in a light insensitive layer of binder. The upper limit can advantageously be kept lower than the concentrations at which colour couplers are used in photographic layers because the compounds according to the invention produce excellent effects even when used in small concentrations.

The DIR compounds according to the invention may be used in any layer of the colour photographic materials, for example in one or more of the light-sensitive silver halide emulsion layers (blue, green or red sensitive) or in a light-insensitive layer adjacent to one of the aforesaid light-sensitive layers. In modern colour photographic multilayered materials it is desired to obtain high interimage effects and an improvement in the graininess and increase in the sharpness by improving the edge effect in all of the colour forming layers. The DIR compounds are preferably used in the red-sensitive or the green-sensitive silver halide emulsion layer or in a light-sensitive layer adjacent thereto, for example a layer situated between the red-sensitive and the green-sensitive layer.

The inhibitory action of the compounds used according to the invention may be produced both in the layer which contains the compounds according to the invention, provided it also contains developable silver halide, and in adjacent silver halide emulsion layers into which the released inhibitor is capable of diffusing. In this way, the compounds according to the invention can be used, for controlling in various directions the development in each of the individual light-sensitive silver halide emulsion layer and, by making use of the vicinal effects which can be achieved with the compounds according to the invention, it is possible to influence the development of one silver halide emulsion layer by the results of image-wise development in another layer so that an overall improvement in graininess, sharpness and colour reproduction can be achieved. The light-sensitive silver halide emulsion layers of the photographic material according to the invention have differing spectral sensitivities and each of these layers is associated with at least one non-diffusible compound for producing an image dye of a colour which is generally complementary to the colour of the spectral sensitivity. These compounds may be conventional colour couplers which are generally incorporated in the silver halide layers. Thus, the red sensitive layer, for example, contains a non-diffusible colour coupler for producing the cyan partial colour image, generally a coupler based on phenol or α-naphthol. The green sensitive layer contains at least one non-diffusible colour coupler for producing the magenta partial colour image, usually a coupler based on 5-pyrazolone or indazolone. The blue sensitive layer unit contains at least one non-diffusible colour coupler for producing the yellow partial colour image, generally a colour coupler having an open chain ketomethylene group. Colour couplers of these kinds are known in large number and have been described in numerous patent specifications, for example in the publication entitled "Farbkuppler" by W. Pelz in "Mitteilungen aus den Forschungslaboratorien der Agfa, Leverkusen/München" Volume III, 111 (1961) and the publication by K. Ventataraman in "The Chemistry of Synthetic Dyes", Vol. 4, 341–387, Academic press 1971.

The non-diffusible colour couplers may contain a substituent which can be split off in the coupling position so that they only require two equivalents of silver halide for colour formation in contrast to the usual 4-equivalent couplers. The colour couplers used are generally themselves colourless but if the releasable substitutent contains a chromophoric group, as in the known masking couplers, the colour couplers generally have a colour which can be used according to current masking techniques for masking unwanted side densities in the image dye. Image dyes produced from colour couplers are generally resistant to diffusion.

If one or more silver halide emulsion layers of the material according to the invention is in the form of a double layer consisting of two partial layers possibly differing from each other in their sensitivity or in their silver:coupler ratio, an arrangement which has already variously been proposed for improving the relationship between sensitivity and graininess, ie., for increasing the sensitivity without coarsening the colour grain (e.g. German Pat. No. 1,121,470; U.S. Pat. No. 3,726,681 and German Offenlegungsschriften Nos. 2,322,165 and 2,416,982), the invention provides that one or both of these partial layers of a double layer may contain one or more of the DIR compounds according to the invention.

If desired, the image dyes may first be produced in a diffusible form during development and then fixed only after transfer to an image receptor layer as is customary in various dye diffusion transfer processes, e.g. those disclosed in U.S. Pat. No. 3,227,550 and No. 3,628,952 and in German Pat. Specification No. 1,772,929. In that case, the light-sensitive silver halide emulsions are associated with colourless or coloured, non-diffusible dye-giving compounds which release diffusible dyes image-wise during development. These dye-giving compounds are incorporated either in the silver halide emulsion layer or in an associated hydrophilic binder layer which may, for example, contain development nuclei and may also contain silver halide which is developable without exposure.

When conventional silver halide emulsions are used in combination with non-diffusible colour couplers or with non-diffusible dye-giving compounds, negative color images are normally obtained. However, both the DIR-compounds according to the invention and the DIR-couplers may advantageously be used in the reversal process by which positive images are obtained. The processes in question include both conventional reversal processes in which the photographic material is first subjected to a process of black-and-white development after imagewise exposure and then color developed after a diffuse second exposure or treatment with fogging agents such as barohydride, and reversal processes in which reversal of the imagewise information takes place in the photographic material due to the presence of the DIR compounds according to the invention. This reversal may take place if, for example, a silver halide emulsion layer which is capable of spontaneous development, ie., development without previous exposure, and which contains a colour coupler or dye-giving compound is arranged adjacent to a conventional silver halide emulsion layer which contains a DIR compound. It is obvious that DIR couplers or DIR compounds used for such a process must be capable of releasing the inhibitor very rapidly so that it will inhibit development imagewise in the spontaneously developable layer.

The non-diffusible colour couplers or dye-giving compounds as well as the non-diffusible development inhibitor releasing compounds preferably used according to the invention are added to the light-sensitive silver halide emulsion or other casting solutions by the usual known methods.

If the compounds are water-soluble or soluble in alkali, they may be added to the emulsions in the form of aqueous solutions, to which water-miscible organic solvents such as ethanol, acetone or dimethylformamide may be added. If the non-diffusible colour couplers, dye-giving compounds or development inhibitor releasing compounds are insoluble in water or alkalies, they may be emulsified in known manner, for example by mixing a solution of these compounds in a low boiling organic solvent with the silver halide emulsion or by first mixing such a solution with an aqueous gelatine solution and then removing the organic solvent in the usual manner and subsequently mixing the resulting gelatine emulsion of the given compound with the silver halide emulsion. If desired, so-called coupler solvents or oil formers may also be used for emulsifying such hydrophobic compounds. These oil formers or coupler solvents are generally higher boiling organic compounds which form oily droplets which enclose the non-diffusible colour couplers and development inhibitor releasing compounds which are to be emulsified in the silver halide emulsion. Information on this topic may be found, for example, in U.S. Pat. Nos. 2,322,027; 2,533,514; 3,689,271; 3,764,336 and 3,765,897. If the compounds according to the invention are emulsified in the layers by means of such oil formers, the groups which confer diffusion resistance to the compounds according to the invention need not be so powerful in their effect since in this case shorter chained alkyl groups such as t-butyl or isoamyl groups are sufficient to prevent diffusion of the compounds according to the invention in the layers of the photographic material. Furthermore, aqueous dispersions of the DIR compounds according to the invention may be prepared and added to the given casting solutions. In this case, aqueous slurries of the compounds are finely milled by vigorous stirring with the addition of sharp sand and/or by the application of ultrasound, optionally in the presence of a suitable hydrophilic binder such as gelatine.

The usual silver halide emulsions may be used in the present invention. The silver halide contained in them may be silver chloride, silver bromide or mixtures thereof, which may have a small silver iodide content of up to 20 mol percent. The emulsions may be either conventional negative emulsions or direct positive emulsions, for example those which have a high sensitivity in the interior of the silver halide grains, e.g. the emulsions described in U.S. Pat. No. 2,592,250.

The binder used for the photographic layers is preferably gelatine but this may be partly or completely replaced by other natural or synthetic binders. Suitable natural binders include e.g. alginic acid and its derivatives such as its salts, esters or amides, cellulose derivatives such as carboxymethylcellulose, alkyl celluloses such as hydroxyethyl cellulose, starch or its derivatives such as ethers or esters, or carrageenates. Polyvinyl alcohol, partially saponified polyvinyl acetate, polyvinyl pyrrolidone and the like are examples of suitable synthetic binders.

The emulsions may also be chemically sensitized, e.g. by the addition of sulphur compounds such as allyl isothiocyanate, allylthiourea, sodium thiosulphate and the like at the chemical ripening stage. Reducing agents may also be used as chemical sensitizers, e.g. the tin compounds described in Belgian Pat. Nos. 493,464 or 568,687, or polyamines such as diethylene triamine or aminomethanesulphinic acid derivatives, e.g. according to Belgian Pat. No. 547,323.

Noble metals such as gold, platinum, palladium, iridium, ruthenium or rhodium and compounds of these metals are also suitable chemical sensitizers. This method of chemical sensitization has been described in the article by R. Koslowsky, Z. Wiss. Phot. 46, 65–72 (1951).

The emulsions may also be sensitized with polyalkylene oxide derivatives, e.g. with a polyethylene oxide having a molecular weight of between 1000 and 20,000, or with condensation products of alkylene oxides and aliphatic alcohols, glycols, cyclic dehydration products of hexitols, alkyl substituted phenols, aliphatic carboxylic acids, aliphatic amines, aliphatic diamines and amides. The condensation products have a molecular weight of at least 700 and preferably more than 1000. Combinations of these sensitizers may, of course, be used for obtaining special effects, as described in Belgian Patent Application No. 537,278 and in British Pat. No. 727,982.

The emulsions may also be spectrally sensitized, e.g. with the usual monomethine or polymethine dyes such as acid or basic cyanines, hemicyanines, streptocyanines, merocyanines, oxonoles, hemioxonoles and styryl dyes, as well as trinuclear or higher nuclear methine dyes such as rhodacyanines or neocyanines. Sensitizers of this kind have been described e.g. in the work by F. M. Hamer "The Cyanine Dyes and Related Compound" (1964), Interscience Publishers John Wiley and Sons.

The emulsions may contain the usual stabilizers such as homopolar or salt-type compounds or mercury containing aromatic or heterocyclic rings such as mercapto triazoles, simple mercury salts, sulphonium mercury double salts and other mercury compounds. Azaindenes are also suitable stabilizers, particularly tetra and pentaazaindenes and especially those which are substituted with hydroxyl or amino groups. Compounds of this kind have been described in the article by Birr, Z.Wiss.Phot. 47, 2-27 (1952). Other suitable stabilizers include, heterocyclic mercapto compounds such as phenyl mercapto tetrazole, quaternary benzothiazole derivatives and benzotriazole.

The emulsions may be hardened in the usual manner, for example with formaldehyde or halogen substituted aldehydes which contain a carboxyl group, such as mucobromic acid, diketones, methanesulphonic acid esters and dialdehydes.

The photographic layers may also be hardened with epoxide type hardeners or hardeners of the tetracyclic ethylene imine or acryloyl series. Examples of such hardeners have been described, for example, in German Offenlegungsschrift No. 2,263,602 and in British Pat. Specification No. 1,266,655. The layers may also be hardened by the process according to German Offenlegungsschrift No. 2,218,009 for producing colour photographic materials suitable for high temperature processing.

The photographic layers or colour photographic multilayered materials may also be hardened with hardeners based on diazine, triazine or 1,2-dihydroquinoline as described in British Pat. Specification Nos. 1,193,290; 1,251,091; 1,306,544 and 1,266,655; French Pat. No. 7,102,716 or German Offenlegungsschrift No. 2,332,317. Examples of such hardeners include diazine derivatives containing alkylsulphonyl or arysulphonyl groups, derivatives of hydrogenated diazines or triazines such as 1,3,5-hexahydrotriazine, fluorosubstituted diazine derivatives such as fluoropyrimidines and esters of 2-substituted 1,2-dihydroquinoline- or 1,2-dihydroisoquinoline-N-carboxylic acids. Vinylsulphonic acid hardeners and carbodiimide or carbamoyl hardeners may also be used, e.g. as described in German Offenlegungsschriften Nos. 2,263,602; and 1,808,685; French Pat. No. 1,491,807; German Pat. No. 872,153 and DDR Pat. No. 7218. Other suitable hardeners have been described, for example, in British Pat. Specification No. 1,268,550.

The materials according to the invention may be, for example, positive, negative or reversal materials mounted on the usual substrates used in known manner for the preparation of photographic materials. Suitable substrates include e.g. foils of cellulose nitrate or cellulose acetate such as cellulose triacetate, polystyrene, polyesters, such as polyethylene terephthalate or polyolefines such as polyethylene or polypropylene, or baryta paper substrates paper substrates laminated with a polyolefine, e.g. a polyethylene or glass.

EXAMPLES

The DIR compounds are preferably used in multilayered units of the kind customarily used e.g. for the preparation of light-sensitive negative or positive colour photographic materials.

The action of the DIR compounds according to the invention will be demonstrated with the aid of an example of a typical arrangement of layers or partial layers used for colour negative materials.

Light-sensitive photographic material:

Arrangement of layers

Support: Substrated cellulose triacetate support.
(a) Intermediate layer of gelatine (1μ)
(b) Cyan layer consisting of an emulsion sensitized to the red region of the spectrum and a colour coupler for cyan (silver application: 4 g of Ag/m$^2$);
(c) Intermediate layer of gelatine (1μ);
(d) magenta layer consisting of an emulsion sensitized to the green region of the spectrum and a colour coupler for magenta (silver application: 3.5 g of Ag/m$^2$);
(e) intermediate layer of gelatine (1μ);
(f) Yellow filter layer (2μ);
(g) Yellow layer consisting of an emulsion which is sensitive to the blue spectral region and a colour coupler for yellow (silver application 1.5 g of Ag/m$^2$);
(h) protective layer of gelatine (1μ).

The material is hardened in the usual manner, e.g. with trisacryloylhexahydrotriazine. The various red(b), green(c) and blue(g) sensitive partial layers are prepared by casting the following solutions:
(b) 1 kg of a red sensitized silver halide emulsion (100 g Ag/kg of emulsion) in which the silver halide consists of 95 mol % of silver bromide and 5 mol % of silver iodide, 50 ml of a 1% solution of 1,3,3a,7-tetraza-4-hydroxyl-6-methylindene in methanol, 360 g of a coupler dispersion of a solution of 15 g of cyan coupler of the following formula:

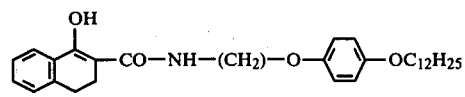

in
7.5 g of dibutylphthalate and
30 g of diethylcarbonate,
100 ml of a 4% aqueous gelatine solution,
0.8 g of Mersolat ® (wetting agent, sulphonated paraffine hydrocarbons),
10 ml of a 10% aqueous saponin solution and
1000 ml of water.
(d) The composition of the casting solution for the green sensitive layer is similar to that used for red sensitive layer (b) except that the emulsion is sensitized to the green region of the spectrum and instead of cyan coupler dispersion it contains 192 g of a dispersion of magenta coupler of the following formula

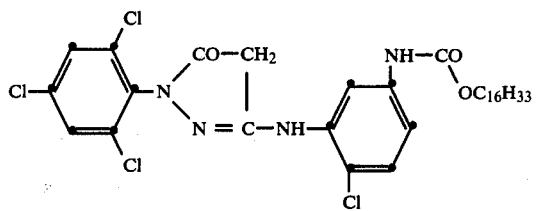

in a composition similar to the dispersion of the cyan coupler of layer b.

(g) The composition of the casting solution for the blue sensitive layer is similar to that of red sensitive layer b except that the emulsion is sensitized only to the blue region of the spectrum and instead of cyan coupler dispersion it contains 175 g of a 5% solution of yellow coupler of the following formula

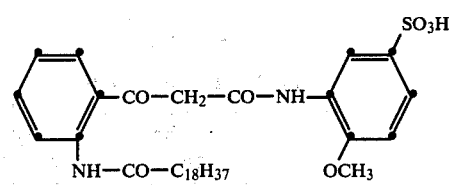

in an aqueous 8% gelatine solution.

Gelatine layers a, c, e and h are prepared by casting the following solution:
125 ml of a 10% gelatine solution,
500 ml of water
5 ml of a 10% aqueous solution of saponin.

The casting solution of the filter yellow layer is the same as the casting solution for gelatine layers a, c, e and h except that it also contains an addition of 1.4 g of finely disperse metallic silver of the kind generally used as barrier filter for the blue spectral portion of light.

Processing

The material is exposed to blue, green and red light behind a grey step wedge and the appropriate colour separation filters in a conventional sensitometer and the exposed material is developed in a colour developer of the following composition:
2 g of sodium salt of isopropanol diaminotetracetic acid
30 g of potassium carbonate
4 g of potassium sulphite
1.5 g of potassium bromide
2 g of hydroxylamine
5 g of colour developer of the following formula

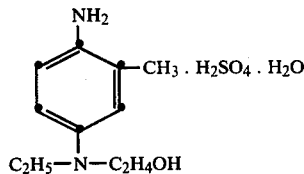

made up to 1 liter. pH adjusted to 10.2.
Development: 3¼ minutes at 38° C.

Each of the subsequent steps of the process indicated below takes 3¼ minutes. The bath temperatures are again 38° C.
Short stop bath
30 ml of acetic acid (concentrated)
20 g of sodium acetate
water up to 1 liter
Rinsing
Bleaching bath
100 g of potassium ferricyanide
15 g of potassium bromide
water up to 1 liter
Rinsing
Fixing bath
20% aqueous solution of sodium thiosulphate
Final rinsing Assessment of the exposed and developed samples:

Since the arrangement of layers prepared for the experiment are not masked, the side densities of the resulting dyes interfere with assessment of the true IIE. To eliminate the interference due to side densities, gradation curves are drawn up from the analytical densities obtained by converting the measured integral densities. The $\gamma$-values on which the IIE measurement is based are obtained from these analytic colour density curves. The IIE is defined as follows:

$$IIE = ((\gamma s - \gamma w)/0.6) \cdot 100\%$$

s: selective exposure
w: white exposure

The graininess is given in $\gamma_D$-values (rms-values obtained with a shutter diameter of 29$\mu$) by the method described by H. T. Buschmann in "Bestimmung der Körnigkeit photographischer Schichten mit Hilfe digitaler Technik" in Optik 38, 1973, pages 169–219.

EXAMPLE 1

Incorporation of DIR compound 2 in red sensitive layer b. DIR compound 2 is dispersed as follows:

A solution of 4.9 g of compound No. 2 in 3 g of tricresylphosphate and 12 ml of ethyl acetate is emulsified in a solution of 100 ml of a 4% aqueous gelatine solution and 0.8 g of Mersolat ® (wetting agent, sulphonated paraffin hydrocarbons) with vigorous stirring by a mixing siren.

Arrangement of layers: consisting of layers a, b and c.
Sample 1: No DIR compound in layer b
Sample 2: Layer b contains DIR compound 2. For preparing the casting solution for the layer, 50 g of the dispersion of DIR compound 2 are added to 1 kg of emulsion.

The samples are exposed to red light behind a step wedge and developed as indicated above. The DIR compound causes regression of the gradation from $\gamma = 1.60$ (Sample 1) to $\gamma = 0.85$ (Sample 2) by inhibition. If the quantities of silver halide or colour coupler used for preparing the comparison sample which has no DIR compound (sample 1a) are reduced so that this sample also has a gradation of 0.85, it is found that the graininess of sample 2 containing the DIR compound is much lower than in Sample 1a in spite of equal gradation and equal sensitivity:

| | Sample 1a | Sample 2 |
|---|---|---|
| Graininess $\delta D \cdot 10^{-2}$ at density | | |

| -continued | | |
|---|---|---|
| | Sample 1a | Sample 2 |
| D = 1 | 2.8 | 1.8 |

EXAMPLE 2

Incorporation of the DIR compound in the magenta layer d of complete layer units (layers a to h):

DIR compound 4 is dissolved in water and the solution is added to the casting solution of d in a quantity corresponding to 2.5 g of DIR compound per kg of emulsion.

For comparison, compound A described in German OS No. 2,405,442 and compound B described in German OS No. 2,359,295 are emulsified in the same molar quantities as DIR compound 4 by the method described in Example 1 and an analogous portion is added to the casting solution of d. For comparison, another sample 4 is prepared which contains no DIR compound in layer d.

The samples were exposed to red, green and white light behind a step wedge and developed as described above.

The activity of the DIR compounds can be seen from the magenta-$\gamma$ values of green exposure (magenta $\gamma_s$). The effect of the DIR compound contained in the magenta layer on the IIE of the cyan layer was also investigated.

| | | IIE % | Exposure | | |
|---|---|---|---|---|---|
| | | | Red | Green | White |
| Sample | DIR compound | cyan | cyan $\gamma_s$ | magenta $\gamma_s$ | cyan $\gamma_w$ |
| 1 | 4 | 117% | 1.50 | 0.61 | 0.20 |
| 2 | A | 28% | 1.47 | 1.15 | 1.30 |
| 3 | B | 42% | 1.45 | 1.11 | 1.20 |
| 4 | — | 25% | 1.45 | 1.35 | 1.30 |

Compound A

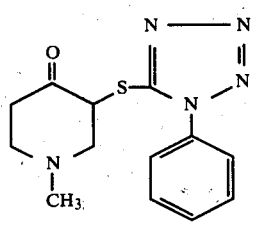

Compound B

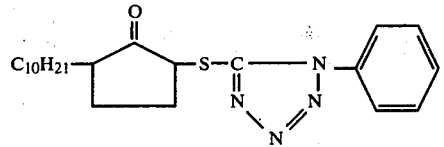

It is clear from the Table (magenta $\gamma_s$) that DIR compound 4 (Sample 1) inhibits most powerfully, i.e. is most active in the magenta layer in which it is incorporated. The other DIR compounds are less active. On exposure to white light, the inhibitor released from DIR compound 4 on development in the magenta layer and diffused into the cyan layer also vigorously inhibits development of the cyan layer so that a strong cyan IIE (117%) is produced. The IIE in the adjacent cyan layer, which is present even without DIR coupler (Sample 4), is increased to a much less extent by DIR compounds A and B.

Similar results are obtained when other compounds according to the invention are used instead of compound 4.

EXAMPLE 3

Incorporation of DIR compounds 4 and 2, the same DIR compound being incorporated both in the magenta layer and in the cyan layer of the complete layer unit a–h. The magenta partial colour layer d is arranged in two partial layers above one another on the principle of double layer arrangements.

The lower layer d1 contains a green sensitized silver halide emulsion in which the silver halide consists of 93 mol % of silver bromide and 7 mol % of silver iodide. This layer contains 35 g of the given magenta coupler to 1 kg of emulsion.

The upper partial layer d2 contains a more sensitive and more coarsely grained green sensitized silver halide emulsion in which the silver halide consists of 95 mol % of silver bromide and 5 mol % of silver iodide. The proportion of magenta coupler in this layer is 10 g to 1 kg of emulsion.

Layer d1 is less sensitive than layer d2 by about 0.5 log I-t units.

DIR compound 4 is dissolved in water whereas DIR compound 2 is emulsified as described in Example 1.

DIR compounds 4 and 2 are added to layer d1 (e.g. 2.5 g of DIR compound 4 to 1 kg of emulsion) and to layer b (e.g. 2.0 g of DIR compound 4 to 1 kg of emulsion) in comparable molar quantities.

The sensitivity of the magenta double layer is higher by 0.2 log I-t units (measured by the criterion of 0.2 density units above fog) than in the individual magenta layer in the total unit according to Example 2 for a comparable graininess.

| Sample | DIR compound in magenta (d1) and cyan (b) layer | IIE % | | Exposure | | | |
|---|---|---|---|---|---|---|---|
| | | cyan | magenta | Red Cyan$_s$ | Green Magenta$_s$ | White Cyan$_w$ | Magenta$_w$ |
| 1 | 4 | 42 | 42 | 0.80 | 0.79 | 0.55 | 0.53 |
| 2 | 2 | 35 | 27 | 0.92 | 0.91 | 0.71 | 0.75 |
| 3 | no DIR | 18 | 10 | 1.35 | 1.40 | 1.24 | 1.34 |

| | DIR compound in magenta (dl) and cyan (b) | IIE % | | Exposure | | | |
|---|---|---|---|---|---|---|---|
| | | | | Red | Green | White | |
| Sample | layer | cyan | magenta | $Cyan_s$ | $Magenta_s$ | $Cyan_w$ | $Magenta_w$ |
| | compond | | | | | | |

-continued

It is clear from the table that when the same DIR compound is used in the red sensitive and the green sensitive partial colour layer, both a high magenta IIE and a high cyan IIE are obtained.

We claim:

1. The color photographic development process for the production of multicolored images by exposing a color photographic multilayered material comprising at least one light-sensitive silver halide emulsion layer and in association with it a non-diffusing color coupler and developing the exposed material with a color developer compound in the presence of a thioether DIR compound which when it reacts with the oxidation product of the color developer compound releases a diffusible substance capable of inhibiting the development of silver halide, wherein the improvement comprises the color development is carried out in the presence of a thioether DIR compound of the following formula I

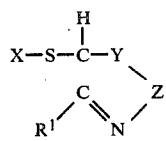

in which
X represents a 5-membered or 6-membered heteroaromatic group having at least one nitrogen atom;
Y represents —O—,

or —S—;
Z represents a —C—C— or —C—N— bond required for completing a 6-membered heterocyclic ring, which may have fused to it a triazole, triazine or benzene ring
$R^1$ represents an aliphatic, araliphatic or aromatic hydrocarbon group, or acyl and
$R^2$ represents hydrogen, an aliphatic, araliphatic or aromatic hydrocarbon group, or acyl.

2. The color photographic development process as claimed in claim 1, in which the color development is carried out in the presence of a non-diffusing thioether compound of the following formula II

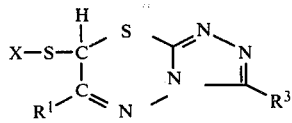

(II)

in which
X and $R^1$ have the meaning indicated in claim 1 and
$R^3$ represents hydrogen, an aliphatic, araliphatic or aromatic hydrocarbon group, or a thioether group and at least one of the groups $R^1$, $R^2$ and $R^3$ is a group which confers diffusion resistance.

3. The color photographic material containing in at least one light-sensitive silver halide emulsion layer or in a light-sensitive layer of binder associated with said light-sensitive emulsion layer, a non-diffusing thioether DIR compound capable of reacting with the oxidation product of a color developer compound to release a diffusing substance which inhibits the development of silver halide, wherein the improvement comprises the DIR compound used is a thioether compound of the following formula I

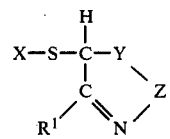

in which
X represents a 5-membered or 6-membered heteroaromatic group having at least one nitrogen atom;
Y represents —O—,

or —S—;
Z represents a —C—C— or —C—N— bond required for completing a 6-membered heterocyclic ring, which may have fused to it a triazole, triazine or benzene ring
$R^1$ represents an aliphatic, araliphatic or aromatic hydrocarbon group, or acyl and
$R^2$ represents hydrogen, an aliphatic, araliphatic or aromatic hydrocarbon group, or acyl.

4. The color photographic material as claimed in claim 3, in which the thioether DIR compound contained in it is a thioether compound of the following formula II

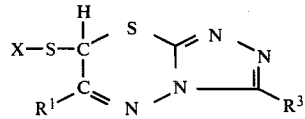

in which
X and $R^1$ have the meaning indicated in claim 3 and
$R^3$ represents hydrogen, an aliphatic, araliphatic or aromatic hydrocarbon group, or a thioether group and at least one of the groups $R^1$, $R^2$ and $R^3$ carries a group which confers diffusion resistance.

5. The color photographic material as claimed in claim 4, in which $R^1$ represents aryl and $R^3$ represents hydrogen or alkyl.

* * * * *